United States Patent [19]

Moran

[11] Patent Number: 5,448,364
[45] Date of Patent: Sep. 5, 1995

[54] PARTICLE DETECTION SYSTEM WITH REFLECTIVE LINE-TO-SPOT COLLECTOR

[75] Inventor: Kevin E. Moran, Belmont, N.C.

[73] Assignee: Estek Corporation, Charlotte, N.C.

[21] Appl. No.: 34,081

[22] Filed: Mar. 22, 1993

[51] Int. Cl.⁶ .......................... G01B 9/02; G01B 11/24; G01N 21/88

[52] U.S. Cl. .................... 356/430; 356/446; 356/432; 356/237; 356/376

[58] Field of Search ............... 356/430, 237, 432, 431, 356/446, 376

[56] References Cited

U.S. PATENT DOCUMENTS

| | | | |
|---|---|---|---|
| 3,575,668 | 4/1971 | Smith | 331/94.5 |
| 3,663,824 | 5/1972 | Blaisdell et al. | 250/219 |
| 3,748,014 | 7/1973 | Belser | 350/7 |
| 3,782,803 | 1/1974 | Buck | 350/7 |
| 3,790,287 | 2/1974 | Cuthbert et al. | 356/120 |
| 3,825,325 | 6/1974 | Hartley et al. | 350/294 |
| 3,843,890 | 10/1974 | Anthony, Jr. et al. | 356/239 |
| 3,900,265 | 8/1975 | Merien et al. | 356/200 |
| 3,961,838 | 6/1976 | Zanoni | 350/7 |
| 3,973,833 | 8/1976 | Lawson | 350/232 |
| 4,054,361 | 10/1977 | Noguchi | 350/7 |
| 4,108,533 | 8/1978 | Sick et al. | 350/6.7 |
| 4,116,527 | 9/1978 | Sick | 350/6.7 |
| 4,158,507 | 6/1979 | Himmel | 356/376 |
| 4,213,157 | 7/1980 | DeBenedictis et al. | 358/293 |
| 4,248,537 | 2/1981 | Sick | 356/431 |
| 4,264,208 | 4/1981 | Haberl et al. | 356/376 |
| 4,314,763 | 2/1982 | Steigmeier et al. | 356/237 |
| 4,321,628 | 3/1982 | Crean | 358/293 |
| 4,355,860 | 10/1982 | Lavallee et al. | 350/6.8 |
| 4,360,275 | 11/1982 | Louderback | 356/446 |
| 4,376,583 | 3/1983 | Alford et al. | 356/237 |
| 4,378,159 | 3/1983 | Galbraith | 356/237 |

(List continued on next page.)

FOREIGN PATENT DOCUMENTS 0178037 4/1986 European Pat. Off. .
180929 4/1987 United Kingdom .
180930 4/1987 United Kingdom .

OTHER PUBLICATIONS

Displays Technology & Applications, Topic—Optics and Laser Technology, Article—Automatic inspection of silicon wafers, From NASA technical support package for technical brief vol. 4, No. 3. NASA, George C. Marshall Space Flight Centere ©1980 IPC Business Press, pp. 319–320.

Journal—Discussions Section, Abstract—Design criteria and performance characteristics of an optical system capable of detecting imperfections on the polished surfaces of semiconductor materials. Authored by J. J. Ruiz, C. S. Williams, and F. A. Padovani. Published Dec., 1974, pp. 689–691.

*Primary Examiner*—Robert P. Limanek
*Assistant Examiner*—Alexander Oscar Williams
*Attorney, Agent, or Firm*—Bell, Seltzer, Park & Gibson

[57] ABSTRACT

The surface inspection system has a scanning head for scanning the laser beam along a predetermined scan line across the surface of an article. A collector receives the light reflected from the article surface along the scan line. The collector has a first mirror position for receiving light reflected from the article surface, a second mirror oriented with respect to the first mirror to receive light reflected from the first mirror, and the first and second mirrors being configured and oriented so as to concentrate the reflected light from a line into a spot. A photodetector is positioned for receiving the thus formed spot of light. The method of inspecting the surface of an article includes the steps of scanning a laser beam along a predetermined scan line across the surface of the article, collectively receiving the light reflected from the article surface along the scan line with a plurality of mirrors so as to concentrate the reflected light from a line into a spot.

32 Claims, 3 Drawing Sheets

U.S. PATENT DOCUMENTS

| | | | |
|---|---|---|---|
| 4,423,331 | 12/1983 | Koizumi et al. | 356/446 |
| 4,568,835 | 2/1986 | Imamura et al. | 356/446 |
| 4,601,576 | 7/1986 | Galbraith | 356/237 |
| 4,630,276 | 12/1986 | Moran | 372/15 |
| 4,655,592 | 4/1987 | Allemand | 356/237 |
| 4,693,601 | 9/1987 | Dabelstein et al. | 356/237 |
| 4,732,473 | 3/1988 | Bille et al. | 356/237 |
| 4,775,238 | 10/1988 | Weber | 356/431 |
| 4,795,911 | 1/1989 | Kohno et al. | 250/572 |
| 4,806,774 | 2/1989 | Lin et al. | 250/550 |
| 4,866,288 | 9/1989 | Weber | 356/431 |
| 4,875,780 | 10/1989 | Moran et al. | 356/446 |
| 4,893,932 | 1/1990 | Knollenberg | 356/369 |
| 4,898,471 | 2/1990 | Stonestrom et al. | 356/394 |
| 5,030,842 | 7/1991 | Koshinaka et al. | 250/571 |
| 5,046,847 | 9/1991 | Nakata et al. | 356/430 |
| 5,076,692 | 12/1991 | Neukermans et al. | 356/538 |
| 5,084,883 | 1/1992 | Khalid et al. | 372/24 |
| 5,088,105 | 2/1992 | Seifres et al. | 372/92 |
| 5,127,726 | 7/1992 | Moran | 356/237 |
| 5,220,403 | 6/1993 | Batchelder et al. | 356/432 |
| 5,278,012 | 1/1994 | Yamanaka et al. | 356/237 |

PARTICLE DETECTION SYSTEM WITH REFLECTIVE LINE-TO-SPOT COLLECTOR

FIELD OF THE INVENTION

This invention relates to surface inspection systems, and more particularly to the inspection of articles, such as silicon wafers, for flaws or defects in the surface of the article.

BACKGROUND OF THE INVENTION

In the process of manufacturing silicon or other semiconductor microchips, light is generally directed through a reticle mask to etch circuits into a silicon wafer. The presence of dirt, dust, smudges or other foreign matter on the surfaces of the reticle mask or the silicon wafer is highly undesirable and adversely affects the resulting circuits. As a result, the reticles and the silicon wafers are necessarily inspected before use. One common inspection technique is for a human inspector to visually examine each surface under intense light and magnification. Debris that is smaller than can be visually detected by the human eye, however, impairs the resulting microchips.

Laser inspection systems therefore have been developed for inspecting the surface of silicon wafers to accurately detect small particles. In these conventional laser inspection systems, light is both specularly reflected and scattered from the surface of an article. The specularly reflected light and the scattered light are both indicative of the presence of particles or flaws on the surface of the article. The light specularly reflected from the surface and the light scattered from the surface are collected and separately relayed to photodetectors such as a photomultiplier tube ("PMT") or a charge coupled device ("CCD").

Several laser inspection systems have been developed which provide various types collectors, such as fiber optic bundles, spherical or parabolic mirrors, elongated lenses, and light pipes, for collecting the light and separately relaying the light to photodetectors. Examples of such systems may be seen in U.S. Pat. No. 4,875,780 by Moran et al. entitled "Method and Apparatus for Inspecting Reticles"; U.S. Pat. No. 4,795,911 by Kohno et al. entitled "Surface Examining Apparatus For Detecting The Presence of Foreign Particles on the Surface"; U.S. Pat. No. 4,630,276 by Moran entitled "Compact Laser Scanning System"; U.S. Pat. No. 4,601,576 by Galbraith entitled "Light Collector For Optical Contaminant And Flaw Detector"; U.S. Pat. No. 4,378,159 by Galbraith entitled "Scanning Contaminant And Defect Detector"; U.S. Pat. No. 4,376,583 by Alford et al. entitled "Surface Inspection Scanning System"; and U.S. Pat. No. 4,360,275 by Louderback entitled "Device for Measurement of Optical Scattering". The collectors of these systems, however, are often bulky and awkward for installation into commercial laser inspection machines and are often inefficient in collecting portions of the light.

Thus, there is a need for a particle detection system which compactly and efficiently collects the light specularly reflected and scattered from the surface of an article and focuses the light into a photodetector.

SUMMARY OF THE INVENTION

The present invention provides a particle detection system having a relatively compact and efficient line-to-spot collector for collecting the specularly reflected or the scattered light from the surface of an article and reflecting the light into a photodetector. The line-to-spot collector has a plurality of mirrors positioned for receiving the light either specularly reflected or scattered from the surface of an article. A first mirror is curved and a second mirror is flat, and the curvature of the first mirror causes the light which is reflected along a scan line from the surface of the article to be focused into a predetermined spot. The configuration and orientation of the mirrors are such that the light reflected or scattered into the line-to-spot collector is compactly and efficiently collected so that the amount of light lost in the transfer process to the photodetector is minimized.

More particularly, the surface inspection system has a scanning mirror for scanning a laser beam along a predetermined scan line across the surface of an article. A collector receives the light reflected from the article surface along the scan line. The collector has a first mirror positioned for receiving light reflected from the article surface and a second mirror oriented with respect to the first mirror to receive light reflected from the first mirror. The first and second mirrors are configured and oriented so as to concentrate the reflected light from a line into a spot. A photodetector is positioned for receiving the thus formed spot of light.

By folding the light path, such that it is reflected from each of the reflective surfaces of the mirrors a plurality of times, it is possible to significantly increase the overall effective length of travel of the specularly reflected or scattered light received by the collector positioned between the scanned article and the photodetector, i.e., the focal length, within a very compact apparatus. The more the light bounces, the shorter the overall length required to efficiently reflect the collected light to the photodetector. The orientation and configuration of the mirrors of the collector thus function like a series of thin lenses, and the actual physical result is a relatively long focal length and a correspondingly large depth of field within a relatively short space.

The light which is reflected from the surface of the article may include both specularly reflected light and diffused or scattered light. These reflected light components or light paths are separately collected by line-to-spot collectors and converted by respective photodetectors to electrical signals for analysis to obtain information about the surface characteristics of the article, such as defects or flaws. This particle detection system may thus be advantageously used for collecting light that is specularly reflected or scattered from the surface of the article.

The surface inspection system of this invention may also provide an underside or edge detector for detecting the light reflected or scattered from an edge of the article. The edge detector may then provide additional information to the collector, such as in the form of a timing signal, about the relative position of the scan line with respect to the article being scanned.

In an alternate embodiment, the specularly reflected light concentrated into a spot may be split into two light paths by a beam splitter, the first light path defining the specular or far field light and the second light path defining the near field light. Separate photodetectors then detect the light from the specular field and the near field to provide additional information about the surface of the scanned article.

The invention also provides a method of inspecting the surface of an article for particles or flaws. The method of inspecting includes the steps of scanning a laser beam along a predetermined scan line across the surface of the article, collectively receiving light reflected from the article surface along the scan line with a plurality of mirrors so as to concentrate the reflected light from a line into a spot.

DESCRIPTION OF THE DRAWINGS

Some of the features and advantages of the present invention having been stated, others will become apparent as the description proceeds when taken in conjunction with the accompanying drawings, in which.

DETAILED DESCRIPTION OF THE ILLUSTRATED EMBODIMENTS

The present invention will be described more fully hereinafter with reference to the accompanying drawings in which illustrated embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 1:
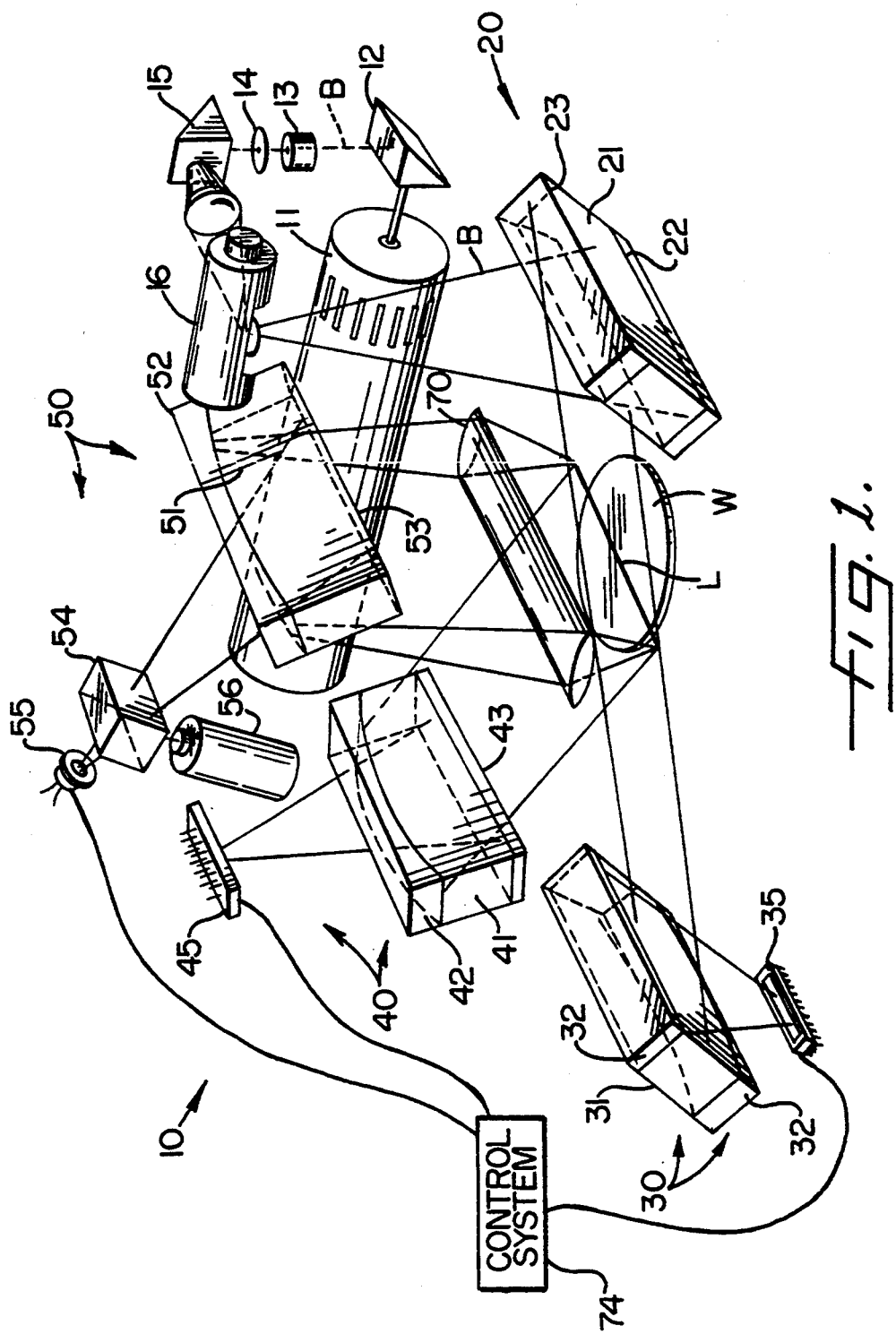
FIG. 1 is a perspective view of a surface inspection system according to the present invention having a line to spot collector for collecting the specularly rejected light, the scattered light, and the edge detected light from an inspected article.
Figure 2:
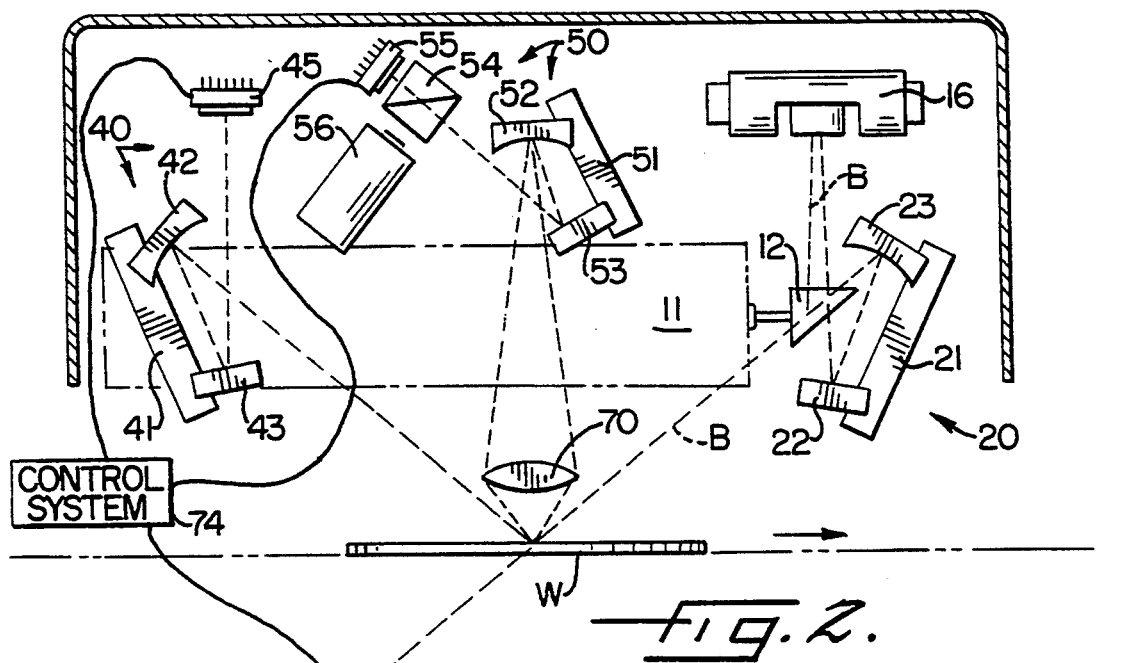
FIG. 2 is a side plan view of the surface inspection system as shown in FIG. 1 according to the present invention having the laser illustrated in phantom lines.

Referring now to the drawings, FIGS. 1 and 2 show a surface inspection system, broadly designated at 10, according to the present invention. A laser 11 generates a laser beam of light, illustrated by dashed lines B, that is reflected and refracted by use of a plurality of mirrors and lenses arranged in a series and designated at 12, 13, 14, and 15. The mirrors and lenses 12, 13, 14, 15 transfer the light B to a scanning head 16. The scanning head 16 has a mirror (not shown) which is mounted for movement to thereby cause the beam of light B to move in a repeating scan pattern and thereby trace a predetermined scan line. The scanning head 16 is preferably an electromagnetic resonant scanner as shown, but other means for scanning the laser beam B apparent to those skilled in the art, such as a polygonal rotating mirror or a piezoelectric scanner, may also be used.

The light B from the scanning head 16, in turn, is transmitted to a folded optical cell 20. The folded optical cell 20 has a housing 21 to which is mounted a flat first mirror 22 positioned for receiving the light B from the scanning head 16 and a curved second mirror 23 oriented with respect to the first mirror 22 to receive the light reflected from the first mirror 22. The first 22 and second mirrors 23 are configured and oriented so as to reflectively form a scan line L across the surface of an article, such as a silicon wafer designated at W. The reflective surfaces of the mirrors 22, 23 are mounted in opposed spaced apart relation to one another so that the laser beam B is reflected from each of the reflective surfaces a plurality of times prior to finally emerging from the cell, whereupon the beam B is directed downwardly onto the surface of the inspection target or article W. The article W may be a wafer formed of silicon or other semiconductor materials or may be another type of article apparent to those skilled in the art.

The number of bounces by the beam B within the folded optical cell 20 can be determined by the entry and exit angles of the scan beam B. By folding the beam B within the folded optical cell 20, such that it is reflected from each of the reflective surfaces a plurality of times, it is possible to significantly increase the overall effective length of travel of the laser beam between the scanning head 16 and the article W, i.e., the focal length, within a very compact apparatus. The folded optical cell 20 thus functions like a series of thin lenses, and the actual physical result is a relatively long focal length and a correspondingly large depth of field within a relatively short space.

By using a concave curved mirror 22 as one of the reflective surfaces of the optical cell 20 in combination with the planar or flat mirror 23, the optical cell 20 also converts the scanning path of the beam B into a substantially collimated or parallel scan. Thus, the scanning beam B remains substantially perpendicular to the inspection surface as it moves across the surface of the article W. Alternatively, the folded optical cell 20 may employ a pair of curved mirrors, and the optical cell can be set to produce either a parallel, a divergent, or a convergent scan pattern. The particular curvature of the curved mirror 22 and the spacing with respect to the flat mirror 23 depend upon the specific details of the particular scanning system. The particular details and spacing arrangement of such a system may be seen in commonly-owned U.S. Pat. No. 4,630,276 which is hereby incorporated herein by reference.

As further illustrated in FIGS. 1 and 2, the laser beam B scans along the predetermined scan line L across the surface of the article W and strikes the article at a predetermined angle of incidence with respect to the surface of the article. The beam B is reflected from the surface of the article W at an angle equal to the angle of incidence. Any defects, debris or irregularities at the surface of the article will cause scattering of the incident beam. Thus, the light B which is reflected from the surface of the wafer W may include both specularly reflected light and diffused or scattered light. These reflected light components or light paths are separately collected by the line-to-spot collectors 40, 50 and converted by respective photodetectors to electrical signals for analysis by a control system 74 to obtain information about the surface characteristics of the article W, such as defects or flaws. Suitable means, such as a conveyor, is provided for advancing the article W along a predetermined path of travel, as indicated by the arrow in FIG. 2, transversely of the scan line L of the laser beam B with the surface of the article W located in a predetermined target plane. The article W is advanced under the laser beam B so that the entire surface of the article W may be scanned.

A line-to-spot collector 40 positioned above the surface of the article W collects the specularly reflected light reflected from the surface of the article W and another line-to-spot collector 50 positioned above the surface of the article W collects the scattered light scattered from the surface of the article W as the article W moves along the predetermined path of travel. A lens 70 positioned above the surface of the article W refracts the light scattered from the surface to thereby more effectively collect the scattered light over a relatively large collection angle as it is directed to the collector 50. The collectors 40, 50 have photodetectors 45, 55, 56, shown in the form of a photomultiplier tube ("PMT") or a charge coupled device ("CCD"), positioned for receiving the collected light. Also, when the laser beam B scans light across the edges of the article W, an edge collector or edge detector 30, located on the opposite side of the article W from the laser scan line, receives the laser beam as it passes beyond the edges of the article W and thus detects the edges of the article W. The edge detector 30 generally provides a timing signal to the control system 74 in order to reference the edges of the article W as it passes along the scan line L. The edge detector 30 may have a similar construction as the line-to-spot collectors 40, 50 and is described in further detail later herein.

Figure 3:
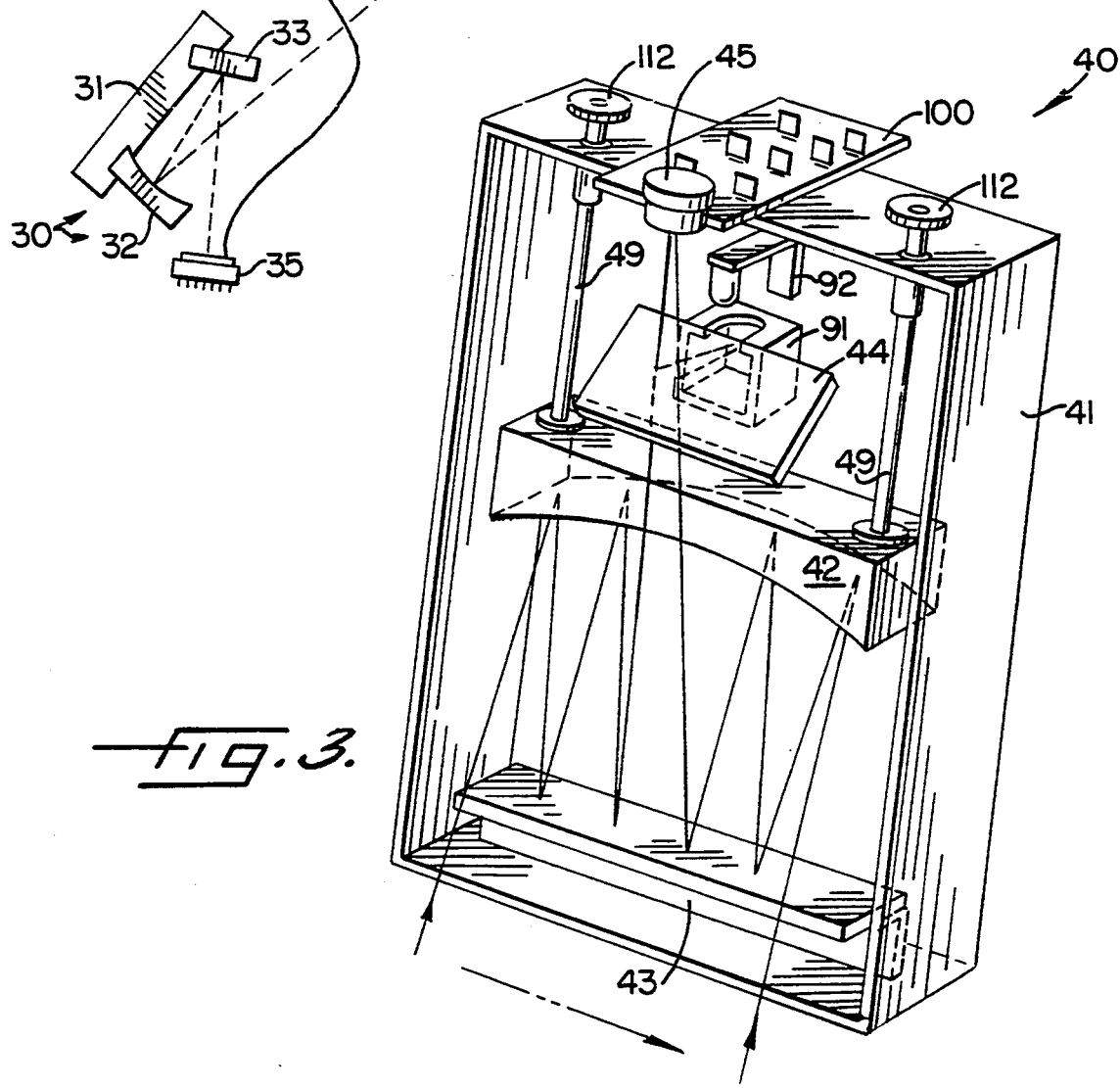
FIG. 3 is a perspective view of the collector and photodetector according to the present invention illustrating the multiple bounces and the folding of the collected light from a line into a spot according to the present invention.

FIG. 3 shows the construction and operation of one of the line-to-spot collectors 40 in greater detail. The specularly reflected light path generally defines a line source of light. The collector 40 receives the line of light reflected from the surface of the article W along the scan line L and concentrates it into a spot at the entrance to photodetector 45. The collector 40 has a housing 41, to which is mounted a relatively curved first mirror 42 positioned for receiving light reflected from the article surface and a relatively flat second mirror 43 and oriented with respect to the first mirror 42 to receive light reflected from the first mirror 42. A pair of adjustment rods 49 connect to the first mirror 42 and the upper portion of the housing 41 and are matingly received by a corresponding pair of adjustment knobs 112, also connected to the upper portion of the housing 41. By use of the adjustment knobs 112 and the adjustment rods 49, the first mirror 42 may be positioned for more effective collection of light reflected from the surface of the article W.

The reflective surfaces of the mirrors 42, 43 of the collector 40 are mounted in opposed spaced apart relation to one another so that the specularly reflected line of light is reflected from each of the reflective surfaces a plurality of times prior to finally emerging from the cell, whereupon the beam B is directed upwardly onto the surface of the photodetector 45. The number of bounces by the beam B within the collector 40 can be determined by the entry and exit angles of the specularly reflected light path. The mirrors 42, 43 thus function as a folded optical cell, similar to the folded optical cell 20 described above except in a reverse orientation. By folding the light path within the collector 40, it is possible to significantly increase the overall effective length of travel of the specularly reflected light between the article W and the photodetector 45, i.e., the focal length, within a very compact apparatus. The more the light bounces between the mirrors 42, 43 the shorter the overall length required to efficiently reflect the collected light to the photodetector 45. The folded optical cell of the collector 40 thus also functions like a series of thin lenses, and the actual physical result is a relatively long focal length and a correspondingly large depth of field within a relatively short space. The curvature of the first mirror 42 in cooperation with the flat second mirror 43 causes the collected light from the scan line L to be focused into a predetermined spot at the photodetector 45. The configuration and orientation of the mirrors 42, 43 are such that the light reflected into the line-to-spot collector 40 is compactly and efficiently collected so that the amount of light lost in the transfer process to the photodetector is minimized. The other line-to-spot collectors 30, 50 shown in FIGS. 1 and 2 are constructed in a manner similar to the collector 40 just described and, therefore, for brevity will not be further described in detail.

Again referring to FIG. 3, the photodetector 45, such as a photomultiplier tube ("PMT") or charge coupled device ("CCD"), for the collector 40 is positioned for receiving the thus formed spot of light. The specularly reflected light component or light path is separately collected and converted by the photodetector 45 to an electrical signal for analysis to obtain information about the surface characteristics of the article W. An optical element or beam splitter 44, such as a silvered mirror, and a light trap 91 may be provided in the light path. The beam splitter 44 and the light trap 91 are oriented in such a manner to prevent light from scattering backwards into the collected light path thereby reducing the background noise received by the photodetector 45. The light trap 91 has a darkened interior surface for absorbing the portion of light split into the light trap 91. An alignment light 92 also cooperates with the light trap 91 and the beam splitter 44 for use in transmitting light in the opposite direction to facilitate alignment of the mirrors 42, 43 so as to collect the specularly reflected light. The photodetector 45 mounts to an electronic circuit board 100 for processing the electrical information transmitted from the photodetector 45 about the surface of the article W.

The collector 50 is positioned above the surface of the article W for collecting the scattered light reflected from the surface of the article W. The scattered light which is diffused from the inspection surface along the scan line L defines a line source of light. The collector 50 is similarly constructed like the collector 40 of FIG. 3 so that the line source of light is concentrated into a spot. The line-to-spot collector 50 for the scattered light as shown in FIGS. 1 and 2, however, has a beam splitter 54 for splitting the light into first and second light paths. The light in the first and second light paths is respectively detected by a first photodetector 55, shown as a CCD, and a second photodetector 56, shown as a PMT. The electrical signals produced from the first and second photodetectors 55, 56 are then combined so as to provide better signal recognition for indicating flaws or defects in the article W. The information collected by the respective photodetectors 45, 54, 55 of the line-to-spot collectors 40, 50 may be processed via suitable interface electronics and computer means 74 (FIG. 1) to provide important information about the nature, severity and location of the defects or flaws present on the surface of the article W.

Referring again to FIGS. 1 and 2, the edge detector 30 is positioned on the underside of the article W for detecting the edges of the article W as it passes through the laser scan line L. Light collected from the edge of the article W is generally collected from a line and is concentrated into a spot for detection.

Like the collectors 40, 50 in the specularly reflected and scattered light paths, the edge detector 30 has a housing 31 with a curved first mirror 32 mounted thereto and positioned for receiving the light from an edge of the article W and a flat second mirror 33 mounted to the housing 31 and so oriented with respect to the first mirror 32 to receive the light from the first mirror 32. The first 32 and second 33 mirrors of the edge detector 30 are also configured and oriented so as to concentrate the reflected light from a line into a spot. A photodetector 35, shown as a CCD, is positioned for receiving the thus formed spot of light. Like the collectors 40, 50, the edge detector 30 has the first mirror 32 preferably curved and the second mirror 33 preferably flat such that the beam B of light has a plurality of bounces between the reflective mirrored surfaces. The collected light from the CCD 35 may then be translated into information, such as a timing signal, about the location of the edges of the wafer W. This information may then be communicated to the reflected and scattered light detection circuits of control system 74 for recognition of edges of the article W relative to the movement the article W along the scan line L. It will be apparent to those skilled in the art that other types of edge detectors may be used in combination with one or more of the collectors 40, 50 for the surface inspection system 10 as described above.

Figure 4:
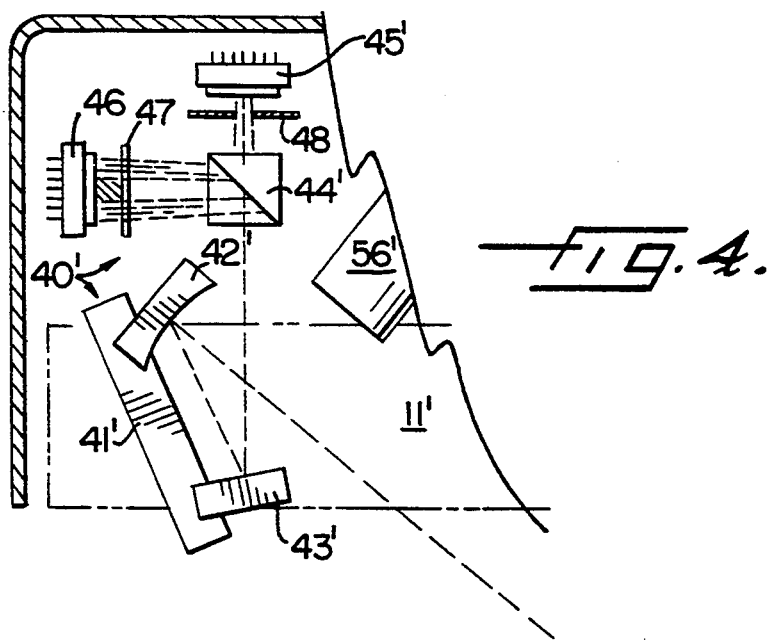
FIG. 4 is a fragmentary side plan view of a second embodiment of the present invention having a near field detector and a specular field detector.
Figure 5:
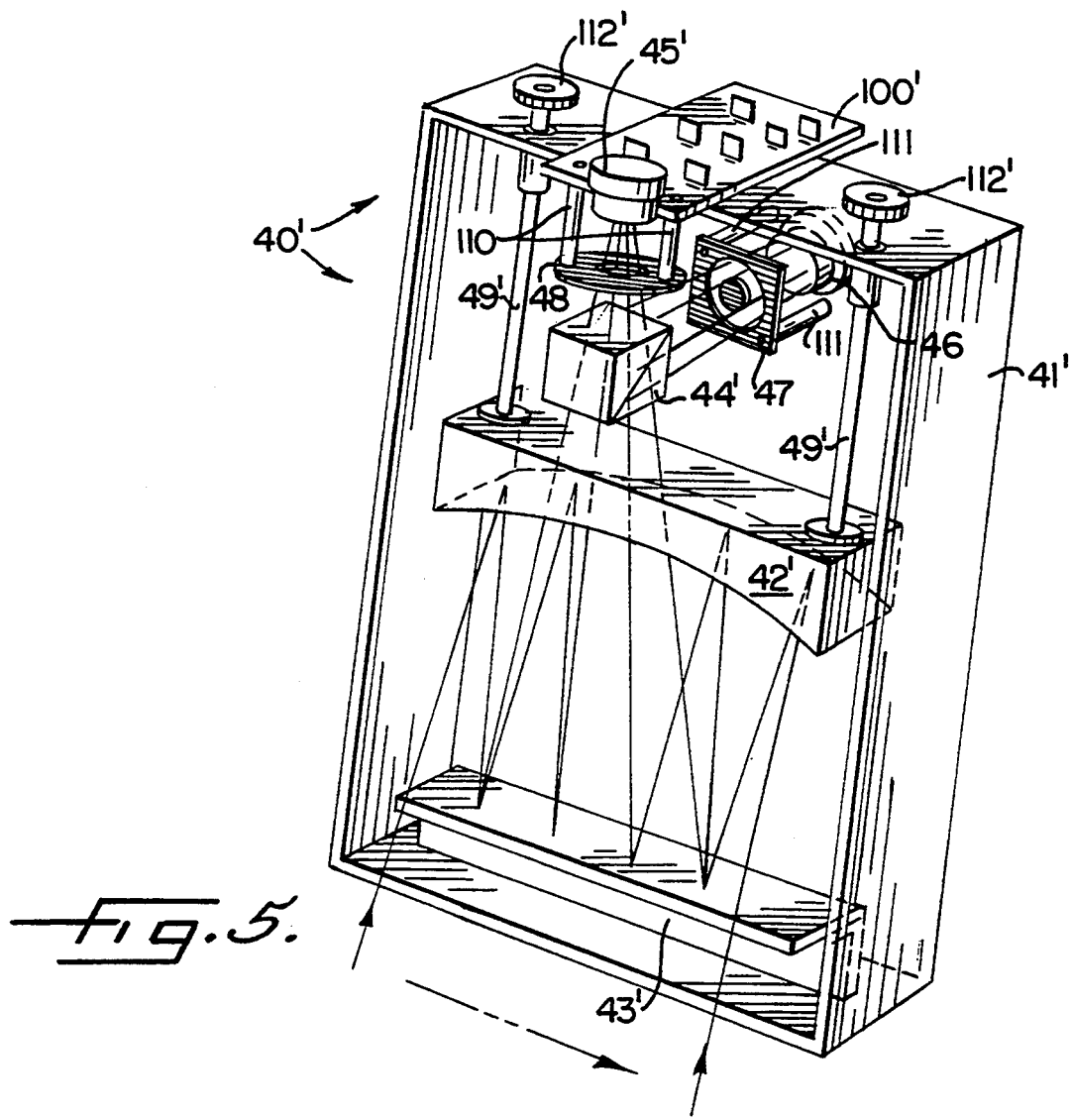
FIG. 5 is a perspective view of a second embodiment of the collector according to the present invention having a near field detector and a specular field detector and illustrating the folding of the collected light from a line into a spot.

A second embodiment of the collector 40' according to the present invention is shown in FIGS. 4 and 5 with like elements of FIGS. 2 and 3 having a prime (') designation. The collector 40' also concentrates the specularly reflected light from a line into a spot similar to the collector 40 described above with reference to FIG. 3. After the collimated light reflects from the mirrors 42', 43', however, the light is split into two photodetectors 45', 46 by a beam splitter 44' wherein one detector 45' detects the specular field of light and the other detector 46 detects the near field of light.

The collector 40' of the second embodiment, as shown in the perspective view of FIG. 5, has a prism 44' for splitting the specularly reflected light received from the second mirror 43'. The split light for the specular field passes through a spatial filter 48 connected to the electronic circuit board 100' by rods 110 and is received by a photodetector 45'. The spatial filter 48 for the specular field is generally rectangular in shape and has a circular opening in a medial portion to provide passage of light through only the medial portion and therefrom to be detected. Light split to the near field passes through a spatial filter 47 connected to the housing 41' by rods 111 and is received by a photodetector 46. The spatial filter 47 for the near field is also generally rectangular in shape, but in contrast to the specular field spatial filter 48, the near field spatial filter 47 has a circular stop in a medial portion and an opening extending around the circular stop to provide passage of light only through the opening around the circular stop. The electrical signals produced from the two photodetectors 45' and 46 may then be combined to improve the signal recognition of defects, particles, or flaws on the surface of the article W, such as the signal-to-noise ratio of the signals.

From the detailed description, and with reference to the drawings, a method of inspecting the surface of a article for particles or flaws is also provided wherein the laser beam B scans along a predetermined scan line L across the surface of the article W. The edges of the article W are detected with the edge detector 30 as the laser beam B scans across the surface thereof. The light reflected from the article surface along the scan line L is collected with the collectors 40, 50 having a plurality of mirrors, such as 42, 43 or 52, 53, so as to concentrate the reflected light from a line into a spot. The thus formed spot of light may then be detected by the photodetectors 45, 54, 55.

In an alternative method, the thus formed spot of light may be split and concentrated into two light paths by a beam splitter 44', such as a silvered mirror, the first light path defining a specular field and the second light path defining a near field. The specular field light and the near field light may then be detected with respective photodetectors, such as 45', 46 shown in FIGS. 4 and 5. The output signal of the specular field photodetector 45' and the output signal of the near field photodetector 46 may be combined to thereby improve the recognition of flaws or defects on the surface of the article W, such as by increasing the signal-to-noise ratio of the electrical signals produced therefrom.

In the drawings and specification, there have been disclosed preferred embodiments of the invention and, although specific terms are employed, they are used in a generic and descriptive sense only and not for the purposes of limitation, the scope of the invention being set forth in the following claims.

That which is claimed is:

1. A surface inspection system, comprising:
   means for scanning a laser beam along a predetermined scan line across the surface of an article;
   a collector for receiving light reflected from the article surface along said scan line, said collector comprising a first mirror positioned for receiving light reflected from the article surface, and a second mirror oriented with respect to said first mirror to receive light reflected from said first mirror, said first and second mirrors being configured and oriented to reflect light from each of the first and second mirrors a plurality of times so as to concentrate the reflected light from a line into a spot; and
   a photodetector positioned for receiving the thus formed spot of light.

2. A surface inspection system according to claim 1, wherein at least one of said mirrors is curved so that the line of reflected light received thereon is focused into a predetermined spot.

3. A surface inspection system according to claim 1, wherein said first mirror is curved and said second mirror is flat, and the curvature of said first mirror causes the light along said scan line to be focused into a predetermined spot.

4. A surface inspection system according to claim 1, further comprising means for splitting the light reflected into a spot into first and second light paths, a second photodetector in addition to said first mentioned photodetector, and wherein said first and second photodetectors detect the respective light from said first and second light paths.

5. A surface inspection system according to claim 4, further comprising a first spatial filter positioned between said beam splitting means and said first photodetector for detecting only the specular field light and a second spatial filter positioned between said beam splitting means and said second photodetector for detecting only the near field light.

6. A surface inspection system according to claim 1, further comprising an edge detector positioned below the underside of the article for detecting the edges of the article as the laser beam scans across the surface thereof.

7. A surface inspection system according to claim 6, wherein said edge detector comprises a first mirror positioned for receiving light scattered from the edges of the article, and a second mirror oriented with respect to said first mirror to receive light reflected from said first mirror, said first and second mirrors being configured and oriented so as to concentrate the reflected light from a line into a spot.

8. A surface inspection system according to claim 1, wherein said laser scanning means comprises a scanning head.

9. A surface inspection system according to claim 8, wherein said laser scanning means further comprises a first mirror positioned for receiving light from said scanning head, and a second mirror oriented with respect to said first mirror to receive light reflected from said first mirror, said first and second mirrors being configured and oriented so as to reflectively form a scan line across the surface of the article.

10. A surface inspection system, comprising:
means for scanning a laser beam along a predetermined scan line across the surface of an article;
a collector for receiving light reflected from the article surface along said scan line, said collector comprising a folded optical cell having a first mirror positioned for receiving light reflected from the article surface, and a second mirror oriented with respect to said first mirror to receive light reflected from said first mirror, at least one of said first and second mirrors being curved, said first and second mirrors of said folded optical cell being configured and oriented to reflect light from each of the first and second mirrors a plurality of times so as to concentrate the reflected light from a line into a spot;
means positionally aligned with said folded optical cell for splitting the concentrated light reflected into a spot into first and second light paths; and
first and second photodetectors positioned for receiving the respective light from said first and second light paths.

11. A surface inspection system according to claim 10, further comprising a first spatial filter positioned between said beam splitting means and said first photodetector for detecting only the specular field light and a second spatial filter positioned between said beam splitting means and said second photodetector for detecting only the near field light.

12. A surface inspection system according to claim 10, wherein said first mirror is curved and said second mirror is flat, and the curvature of said first mirror causes the light along said scan line to be focused into a predetermined spot.

13. A surface inspection system according to claim 10, wherein said laser scanning means comprises a scanning head.

14. A surface inspection system according to claim 13, wherein said laser scanning means further comprises a first mirror positioned for receiving light from said scanning head, and a second mirror oriented with respect to said first mirror to receive light reflected from said first mirror, said first and second mirrors being configured and oriented so as to reflectively form a scan line across the surface of the article.

15. A surface inspection system according to claim 10, further comprising an edge detector positioned below the underside of the article for detecting the edges of the article as the laser beam scans across the surface thereof.

16. A surface inspection system according to claim 15, wherein said edge detector comprises a first mirror positioned for receiving light scattered from the edges of the article, and a second mirror oriented with respect to said first mirror to receive light reflected from said first mirror, said first and second mirrors being configured and oriented so as to concentrate the reflected light from a line into a spot.

17. A surface inspection system, comprising:
means for scanning a laser beam along a predetermined scan line across the surface of an article, said laser scanning means comprising a scanning head, a first mirror positioned for receiving light from said scanning head, and a second mirror oriented with respect to said first mirror to receive light reflected from said first mirror, said first and second mirrors being configured and oriented to reflect light from each of the first and second mirrors a plurality of times so as to reflectively form the scan line across the surface of the article;
an edge detector positioned below the underside of the article for detecting the edges of the article as the laser beam scans across the surface thereof;
a collector for receiving light reflected from the article surface along said scan line, said collector comprising a first mirror positioned for receiving light reflected from the article surface, and a second mirror oriented with respect to said first mirror to receive light reflected from said first mirror, said first and second mirrors being configured and oriented so as to concentrate the reflected light from a line into a spot; and
a photodetector positioned for receiving the thus formed spot of light.

18. A surface inspection system according to claim 17, wherein said edge detector comprises a first mirror positioned for receiving light scattered from the edges of the article, and a second mirror oriented with respect to said first mirror to receive light reflected from said first mirror, said first and second mirrors being configured and oriented so as to concentrate the reflected light from a line into a spot.

19. A surface inspection system according to claim 17, wherein at least one of said mirrors is curved so that the line of reflected light received thereon is focused into a predetermined spot.

20. A surface inspection system according to claim 17, wherein said first mirror is curved and said second mirror is flat, and the curvature of said first mirror causes the light along said scan line to be focused into a predetermined spot.

21. A surface inspection system according to claim 17, further comprising means for splitting the light reflected into a spot into first and second light paths, a second photodetector in addition to said first mentioned photodetector, and wherein said first and second photodetectors detect the respective light from said first and second light paths.

22. A surface inspection system according to claim 21, further comprising a first spatial filter positioned between said beam splitting means and said first photodetector for detecting only the specular field light and a second spatial filter positioned between said beam splitting means and said second photodetector for detecting only the near field light.

23. A surface inspection system, comprising:
means for scanning a laser beam along a predetermined scan line across the surface of an article; and
an edge detector positioned below the underside of the article for detecting the edges of the article as the laser beam scans along the surface thereof, said edge detector comprising a first mirror positioned for receiving light scattered from the edges of the article, and a second mirror oriented with respect to said first mirror to receive light reflected from said first mirror, said first and second mirrors being configured and oriented so as to concentrate the reflected light from a line into a spot.

24. A surface inspection system according to claim 23, wherein said edge detector further comprises a photodetector positioned adjacent said first and second mirrors for receiving the thus formed spot of light.

25. A surface inspection system according to claim 23, wherein said laser scanning means comprises a scanning head.

26. A surface inspection system according to claim 25, wherein said laser scanning means further comprises a first mirror positioned for receiving light from said scanning head, and a second mirror oriented with respect to said first mirror to receive light reflected from said first mirror, said first and second mirrors being configured and oriented so as to reflectively form a scan line across the surface of the article.

27. A surface inspection system, comprising:
means for scanning a laser beam along a predetermined scan line across the surface of an article, said laser scanning means comprising a scanning head, a first mirror positioned for receiving light from said scanning head, and a second mirror oriented with respect to said first mirror to receive light reflected from said first mirror, said first and second mirrors being configured and oriented so as to reflectively form the scan line across the surface of the article;
an edge detector positioned below the underside of the article for detecting the edges of the article as the laser beam scans along the surface thereof, said edge detector comprising a first mirror positioned for receiving light scattered from the edges of the article, and a second mirror oriented with respect to said first mirror to receive light reflected from said first mirror, said first and second mirrors being configured and oriented so as to concentrate the reflected light from a line into a spot; and
a photodetector positioned adjacent said first and second mirrors of said edge detector for receiving the thus formed spot of light.

28. A method of inspecting the surface of a article for particles or flaws, comprising the steps of:
scanning a laser beam along a predetermined scan line across the surface of a article; and
collectively receiving light reflected from the article surface along the scan line with a plurality of mirrors being configured and oriented to reflect light from each of the plurality of mirrors a plurality of times so as to concentrate the reflected light from a line into a spot.

29. A method according to claim 28, further comprising the step of detecting the concentrated light with a photodetector so as to determined the presence of particles or flaws on the surface of the article.

30. A method according to claim 28, further comprising the steps of:
splitting the concentrated light into two light paths;
filtering the two light paths so as to define a specular field and a near field; and
detecting the specular field light and the near field light with respective photodetectors.

31. A method according to claim 28, further comprising the step of:
detecting the edges of the article as the laser beam scans across the surface thereof.

32. A method of inspecting the surface of a article for particles or flaws, comprising the steps of:
scanning a laser beam along a predetermined scan line across the surface of an article;
detecting the edges of the article as the laser beam scans across the surface thereof;
collectively receiving light reflected from the article surface along the scan line with a plurality of mirrors so as to concentrate the reflected light from a line into a spot;
splitting the concentrated light into two light paths;
filtering the two light paths so as to define a specular field and a near field;
detecting the specular field light and the near field light with respective photodetectors; and
combining the output of the specular field photodetector and the output of the near field photodetector to thereby improve the recognition of flaws or defects on the surface of the article.

* * * * *